United States Patent
Mayer et al.

(10) Patent No.: US 8,226,411 B2
(45) Date of Patent: Jul. 24, 2012

(54) METHOD FOR AFFIXING AN ARTIFICIAL ELEMENT TO A SURFACE OF DENTINE, ENAMEL, BONE, OR A CORRESPONDING SUBSTITUTE MATERIAL, AND SET FOR CARRYING OUT THE METHOD

(75) Inventors: Jörg Mayer, Niederlenz (CH); Andrea Müller, Winterthur (CH); Urs Weber, Evilard (CH)

(73) Assignee: Woodwelding AG, Stansstad (CH)

( * ) Notice: Subject to any disclaimer, the term of this patent is extended or adjusted under 35 U.S.C. 154(b) by 303 days.

(21) Appl. No.: 12/521,217

(22) PCT Filed: Dec. 11, 2007

(86) PCT No.: PCT/CH2007/000620
§ 371 (c)(1),
(2), (4) Date: Aug. 10, 2009

(87) PCT Pub. No.: WO2008/080239
PCT Pub. Date: Jul. 10, 2008

(65) Prior Publication Data
US 2010/0081110 A1    Apr. 1, 2010

Related U.S. Application Data

(60) Provisional application No. 60/882,252, filed on Dec. 28, 2006.

(51) Int. Cl.
*A61C 5/00*    (2006.01)
(52) U.S. Cl. ...................................... 433/215
(58) Field of Classification Search .................. 433/215, 433/3, 9, 169, 172–176, 180, 226; 156/73.1, 156/580.1
See application file for complete search history.

(56) References Cited

U.S. PATENT DOCUMENTS

| | | | |
|---|---|---|---|
| 3,462,839 A | | 8/1969 | Boyer et al. |
| 4,566,138 A | | 1/1986 | Lewis et al. |
| 4,975,059 A | * | 12/1990 | Sendax .......................... 433/173 |
| 5,709,548 A | | 1/1998 | Oxman et al. |
| 5,746,856 A | * | 5/1998 | Hendershot et al. ......... 156/73.4 |

(Continued)

FOREIGN PATENT DOCUMENTS

WO    99/52478    10/1999

(Continued)

*Primary Examiner* — Cris L Rodriguez
*Assistant Examiner* — Mirayda A Aponte
(74) *Attorney, Agent, or Firm* — Rankin, Hill & Clark LLP

(57) ABSTRACT

Elements (5) such as dental fillings, inlays, dental veneers, root pins, implants to be implanted in bone tissue, or endoprostheses are affixed to surfaces (3) of dentine, tooth enamel, bone tissue, or a corresponding substitute material, by providing the element with element surfaces (6) including a first thermoplastic material, by equipping the surfaces (3) of dentine, tooth enamel, bone tissue, or a corresponding substitute material in a preparatory step in such a way that they become weldable with the first thermoplastic material, and by welding the element surfaces (6) to the pre-treated surfaces (3) by e.g. exciting the appropriately positioned element (5) with mechanical vibrations. The pre-treatment of the surfaces (3) in the preparatory step is achieved by attaching solid bodies (2) including a second thermoplastic material to the surfaces (3), with the aid of a curable compound (generally known for preparatory treatment of dentine or enamel surfaces) or with the aid of a cement.

25 Claims, 2 Drawing Sheets

U.S. PATENT DOCUMENTS

| | | | |
|---|---|---|---|
| 5,773,794 A * | 6/1998 | Zimet-Sternberg et al. | 219/440 |
| 6,133,339 A * | 10/2000 | Xie et al. | 523/116 |
| 6,709,526 B1 * | 3/2004 | Bailey et al. | 127/29 |
| 6,955,540 B2 * | 10/2005 | Mayer et al. | 433/169 |
| 2004/0197311 A1 * | 10/2004 | Brekke et al. | 424/93.7 |

FOREIGN PATENT DOCUMENTS

| | | |
|---|---|---|
| WO | 02/069817 | 9/2002 |
| WO | 2004/017857 | 3/2004 |
| WO | 2005/079696 | 9/2005 |
| WO | 2007/092869 | 8/2007 |

* cited by examiner

METHOD FOR AFFIXING AN ARTIFICIAL ELEMENT TO A SURFACE OF DENTINE, ENAMEL, BONE, OR A CORRESPONDING SUBSTITUTE MATERIAL, AND SET FOR CARRYING OUT THE METHOD

BACKGROUND OF THE INVENTION

1. Field of the Invention

The invention lies in the field of medical technology and concerns a method and a set according to the generic terms of the corresponding independent claims. The method serves the affixing or fastening of an artificial element to a surface of dentine, tooth enamel, bone tissue, or of a corresponding substitute material. The set serves for carrying out the method and comprises the element to be affixed and/or a preparation, wherein the preparation is applied to the surfaces, or to the element, prior to the positioning and affixing of the element.

2. Description of Related Art

It is well known in dentistry to make e.g. fillings, inlays, or dental veneers from composite materials. These composite materials usually comprise a curable matrix material and filler materials contained in the matrix material. The composite materials are applied in the form of a paste to the surface where they are to adhere and they are cured in situ. The matrix material is e.g. a polymer which is curable by cross-linking, it is e.g. based on polymethacrylate or polymethylmethacrylate, wherein the in-situ curing is initiated by ultraviolet light. The filler material is e.g. a ceramic material, a glass-ceramic, or a glass, and is contained in the matrix material as e.g. particles, fibers, or whiskers.

In order to achieve an effective bond between the aforementioned composite materials and the dentine or enamel surfaces of the tooth, these surfaces are pre-treated. For this preparatory treatment e.g. etching agents, sealing agents, adhesion promoters and/or adhesion agents are used, which are either applied in succession (e.g. adhesive systems of conditioner, primer, and adhesive) or which are contained within a single primer preparation requiring just one application. One of the purposes of the preparatory treatment is to render the inherently hydrophilic dentine and enamel surfaces receptive to the usually hydrophobic composite material to be adhered to it, to create covalent or ionic bonds with molecules of the dentine or enamel surface, and to provide molecules capable of covalent or ionic bonding between the pre-treated surface and the material to be attached to it. Corresponding molecules and preparations belong to the state-of-the-art technology.

Usually at least one of the pre-treatment preparations comprises a polymer which is curable by cross-linking and/or corresponding monomers or oligomers, wherein this polymer is adapted to the matrix material of the composite material to be affixed to the pretreated surface in such a way that cross-linking between components of the pre-treatment preparation and the matrix material becomes possible.

The aforementioned pre-treatment preparations are usually applied to the dentine or enamel surface in one or several steps of preparatory treatment and, if necessary, partly cured. Then the composite material is applied to the pre-treated dentine or enamel surface and the composite material is cured, wherein not fully cured components of the pre-treatment preparation are also completely cured.

It is also a known practice to affix implants to bones or bone sections, wherein a bone cement is applied between the implant and the bone or bone section. Such cements are also solidifiable (curable) and fulfill similar functions as the aforementioned pre-treatment preparation used in dentistry. The cements can be polymer, ceramic or hydraulic cements and usually also contain filler materials.

Another procedure known e.g. from the publications WO 02/069 817, WO 2004/017 857, and WO 2005/079 696, is to fasten elements, consisting at least in part of thermoplastic material, to surfaces of bone tissue, dentine, or tooth enamel, by pressing the element against said surfaces and exciting it with mechanical vibration, e.g. ultrasonic vibration, so that the thermoplastic material is softened at the contact surfaces and pressed into pores and surface irregularities of the bone tissue, dentine, or enamel, in order to form a form-fit connection after re-solidification. This method has the important advantages that there is no need for a preparatory treatment of the surfaces and that, compared to the method using curable composite materials as briefly mentioned above, causes less or practically no shrinkage.

BRIEF SUMMARY OF THE INVENTION

The object of the invention is to create a further method by which an artificial element can be affixed to a surface of dentine, tooth enamel, bone tissue, or a corresponding substitute material. The fixations created by the method according to the invention are to have similar stabilities as the known fixations as briefly described above. It is a further object of the invention to create a set for carrying out the method.

These objects are achieved by the method and the set as defined in the corresponding independent claims.

The principle of the method according to the invention is based on the one hand on making the element to be affixed to the surface of dentine, tooth enamel, bone tissue, or a corresponding substitute material, at least in the areas of its surface where the fixation is to be achieved, at least partly of a first thermoplastic material. On the other hand the surfaces, to which the element is to be attached, are pre-treated to be able to be welded together with the first thermoplastic material. The element is then attached to the pre-treated surfaces by such a welding process. The heat necessary for the welding step e.g., is applied to the element and/or to the pretreated surface or it is created by irradiating one of the two or by friction between the two, e.g. through mechanical vibration as known e.g. from ultrasonic or friction welding. Preferably, mechanical vibration having a frequency of between 2 and 200 kHz is applied to the element.

It is shown that the named pre-treatment of the surfaces of dentine, tooth enamel, bone tissue, or a corresponding substitute material, can be achieved by using a generally known or functionally similar pre-treatment preparation including at least one curable component in combination with solid bodies including a second thermoplastic material, wherein the solid bodies are attached to said surfaces essentially by means of the curable components of the preparation. The solid bodies are e.g. particles, fibers, or constitute a flat—possibly three-dimensional—item and they consist entirely of the second thermoplastic material, include in addition to the second thermoplastic material a filler, or are coated with the second thermoplastic material. For the preparatory treatment the solid bodies including the second thermoplastic material are either already blended with other components of the pre-treatment preparation and/or they are contacted with these in situ. Where the surface to be pre-treated is a substitute material, it is also possible to perform the preparatory treatment ex situ and to connect the pre-treated substitute material with a further element in situ by means of mechanical vibrations.

The pre-treatment preparation is applied to the relevant surfaces prior to the positioning of the element to be affixed thereto and prior to the welding process, and it is cured to such an extent that the solid bodies including the second thermoplastic material adhere firmly to the surface of dentine, tooth enamel, bone tissue, or the corresponding substitute material. Curing of the pre-treatment preparation before welding may be a complete curing or possibly a partial curing only, with completion of the curing to be effected during or after the welding process.

The pre-treatment preparation being modified according to the invention has a function regarding the surface of dentine, tooth enamel, bone tissue, or the corresponding substitute material, which is substantially the same as the function of per se known pre-treatment preparations as briefly described further above. With regard to the element to be attached, the connecting function is taken over substantially fully by the solid bodies including the second thermoplastic material. Other than the generally known preparations, the pre-treatment preparation of the invention may contain additional molecules, which during the curing process cause e.g. covalent bonds between the cured matrix material and the solid bodies including the second thermoplastic material. The expert is familiar with such molecules. They are advantageously provided on the solid bodies.

For instance, for affixing an element of polyamide, solid bodies of polyamide are provided in the pre-treatment preparation while the matrix material is a two-component epoxy system. To enable the polyamide solid bodies to be bound firmly into the matrix material when the epoxy resin is cured, the bodies are e.g. silanized prior to being introduced into the matrix material.

When selecting size and quantity of solid bodies including the second thermoplastic material, care needs to be taken that they are available on the pre-treated surfaces in sufficient numbers and with sufficient sizes and that they are sufficiently accessible for being able to be reliably welded. This can be achieved e.g. if the smallest dimensions of the solid bodies are greater than the thickness of a layer to be formed by the other components of the pre-treatment preparation. Experiments further show that the smallest dimensions of the solid bodies comprising the second thermoplastic material are to be at least 2 µm, advantageously 20 µm. It appears that smaller solid bodies produce inferior welded connections, which may be due to the solid bodies being torn from the pre-treated surface by the mechanical vibrations used for welding or not being able to be softened or melted by this vibration. Experiments also show that a cured layer of the other components of the pre-treatment preparation which layer covers the solid bodies, i.e. extends between the second thermoplastic material of the solid bodies and the first thermoplastic material of the element to be affixed, does not have any negative effects upon the welding process. This seems to be due to such a layer simply being scraped off, broken up, or removed in some other way, prior to the actual welding, and the debris of the layer being integrated in the molten phase without negative effect on the weld which is achieved.

For achieving a sufficiently stable connection between the pretreated surface and the element of e.g. 10 to 15 N/mm2 at a weld stability of 50-100 N/mm2, it is necessary for the particles to constitute 10 to 20% of the pretreated surface. From such calculation and a known size of the solid bodies and a known thickness of the pretreatment layer, the number of solid bodies to be provided per volume of pretreatment preparation can be estimated.

The second thermoplastic material of the solid bodies of the pre-treatment preparation and the first thermoplastic material of the element to be affixed are matched in such a manner that they are capable of being welded together. As the expert in the field of bonding plastic materials by means of ultrasound or friction is well aware, this implies that both thermoplastic materials have similar melting temperatures and similar viscosities when liquefied and that they are capable of mutual wetting and/or mixing. Advantageously, they both belong to the same class of thermoplastics or are indeed the same thermoplastic. An example of different thermoplastics being capable of being welded together are polycarbonate and polymethylmethacrylate. Other pairings of two different, but weldable thermoplastic materials are disclosed e.g. in "Plastics and Composites Welding Handbook, Eds David A. Grewell, Avraham Benatar, Joon B. Park; Hanser Munich, 2003 pp 177-179.

Pairs of thermoplastic materials are weldable through compatibility, i.e. they form one mixed molten phase, or through blending, i.e. the two materials remain separate in the molten phase but mechanically intermingled, wherein the intermingeling is enhanced through high shearing forces during the welding process and similar viscosities of the two molten materials. The lower the compatibility of the two materials are, the more it becomes necessary for weldability that the molecular weights of the two materials are such adapted to each other that the two materials have similar shearing viscosities at similar temperatures.

Examples of pairs of thermoplastic materials which are suitable for being used in connection with the invention are the following (advantageously of two different materials the first named material is used for the element and the second named material for the solid particles):

polyether ketone and polyether imide (compatible)
polycarbonate and acryl-butadiene-styrene (compatible)
polyamide 12 and polyamide 11 (compatible)
Polyamide 6, 6/6, or 6/4 and any one of polyamide 6, 6/6, or 6/4 (compatible)
Polyether imide and polycarbonate (blending)
Polysulfone and polycarbonate (blending)
Polycarbonate and ABS, polyacrylene, polyether imide, or polysulfone (blending)
polyamide 12 or 11 and polyamide 6, 6/6 or 6/4 (blending)
PVC rigid and ABS (blending)

Examples of elements which can be advantageously attached to surfaces of dentine, tooth enamel, or corresponding substitute materials (e.g. ceramic materials of dental implants such as zirconiumoxide or ceramics based on calcium phosphate) using the method according to the invention, are fillings to be fixed in tooth cavities, dental veneers or inlays to be fastened on appropriately prepared teeth, crowns, bridges, or partial prostheses to be mounted on tooth stumps, fittings for dental corrections or jewelery to be fastened to teeth, or root pins to be secured in dental roots.

Examples of elements, which can be advantageously attached to surfaces of bone tissue or corresponding substitute materials (e.g. bone replacement materials based on calcium phosphate) with the method according to the invention, are implants (e.g. dental implants), endoprostheses, or therapeutic elements e.g. equipped to release a therapeutic agent.

Said elements may consist entirely of the first thermoplastic material, wherein this material may further comprise filler materials in varying concentrations. Alternatively, the first thermoplastic material may only be provided on those surface areas of the element, which are to come into contact with the pre-treated surfaces, while other areas consist e.g. of metal, ceramics, or glass.

Thermoplastic materials suitable on the one hand for elements to be fastened to surfaces of dentine, tooth enamel, bone tissue, or corresponding substitute materials, and on the other hand for the solid bodies of the corresponding pre-treatment preparation, may or may not be resorbable, depending on the application. Resorbable materials are e.g. polymers based on lactic and/or glycolic acid (PLA, PLLA, PGA, PLGA, etc.), polyhydroxy alkanoates (PHA), polycaprolactone (PCL), polysaccharides, polydioxanons (PD), polyanhydrides, polypeptides, or corresponding copolymers or mixed polymers. Non-resorbable polymers are e.g. polyolefins, polyacrylates, polymethacrylates, polycarbonates, polyamides, polyesters, polyurethanes, polysulphones, polyarylketones, polyetherketones, polyetherimides, polyamides, acryl-butadiene-styrene, polyphenylsulphides, liquid-crystal polymers (LCP), polyacetales, halogenated polymers (in particular halogenated polyolefins, polyphenylsulphides, polysulphones), polyether, PVC, ABS or corresponding copolymers and mixed polymers. As already mentioned above, these materials can also be used in a filled state (composite materials) in the element to be affixed and/or in the solid bodies of the pre-treatment preparation.

The set according to the invention includes the element to be affixed, or at least the solid bodies of the pre-treatment preparation (and preferably further components thereof), or both. It further includes information on the use of mechanical vibrations for the affixation. If the set includes only the element to be affixed, it contains, in addition, information on which pre-treatment preparations are to be used in combination with the element, in particular with regard to the second thermoplastic material of the solid bodies contained in, or used with the pre-treatment preparation. If the set includes only the pre-treatment preparation with the solid bodies or only the solid bodies, it contains, in addition, information on what kind of element is to be used in combination with the preparation, in particular with regard to the first thermoplastic material, which the element is to comprise.

BRIEF DESCRIPTION OF THE DRAWINGS

The principle of the method according to the invention and exemplary applications thereof are described in detail in connection with the following Figs., wherein.

DETAILED DESCRIPTION OF THE INVENTION

Figures 1A, 1B, 1C, 1D:
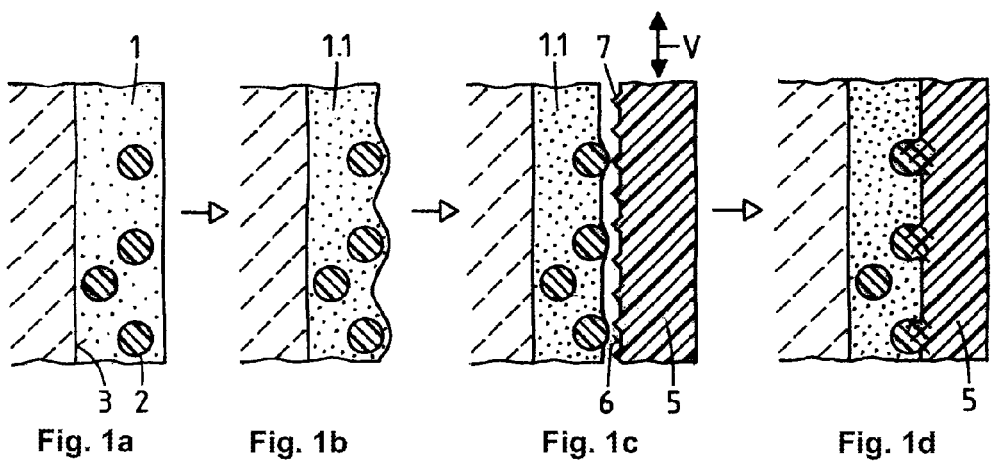
FIG. 1a shows, in section, a pre-treatment preparation applied to the surface of a dental dentine.
FIG. 1b shows, in section, the pre-treatment preparation applied to the surface of a dental dentine after the step of curing.
FIG. 1c shows, in section, the cured pre-treatment preparation and an element to be affixed to the dentine.
FIG. 1d shows, in section, the cured pre-treatment preparation and the affixed element.

FIGS. 1a-1d show a first exemplary embodiment of the method according to the invention. The method consists essentially of applying the liquid or paste-like pre-treatment preparation 1—containing a curable component and the solid bodies 2 (in this case particles) comprising the second thermoplastic material—to the surface 3 of dentine, tooth enamel, bone tissue, or the corresponding substitute material, of sufficiently curing the curable component of the pre-treatment preparation 1 by suitable means (e.g. UV light, heat, time), of bringing the element 5 to be affixed into contact with the pre-treated surface, i.e. the surface of the cured pre-treatment preparation 1.1, and of vibrating, which results in the connection between the cured pre-treatment preparation 1.1 and the element 5, as illustrated schematically in FIG. 1d. This connection is based on a welded connection between the first thermoplastic material of the element 5 and the second thermoplastic material of the solid bodies 2 embedded in the cured pre-treatment preparation 1.1.

Instead of generating the heat necessary for melting and welding together the first and second thermoplastic material, it is possible to, instead of vibrating the element and therewhich create friction between the element and the surface to which it is to be welded, to position the element in a heated (e.g. molten) state against the surface or to provide radiation (e.g. light) absorbing fillers in one or both of the thermoplastic materials and heat the welding location by corresponding irradiation. It is possible also to heat the material comprising a suitable filler by induction heating.

During application and/or curing, a corresponding and generally known chemistry of the pre-treatment preparation causes reactions with molecules of the surface 3, which results in a firm adhesion between said surface 3 and the cured pre-treatment compound 1.1. The solid bodies 2 comprising the second thermoplastic material are possibly held only mechanically in the at least partially cured pre-treatment preparation 1.1. But it is also possible to additionally equip the pre-treatment preparation and/or the solid bodies to provoke reactions (e.g. cross-linking reactions) with the surfaces of the solid bodies during curing, binding the solid bodies covalently or ionically to other components of the pre-treatment preparation, in particular to the curable component thereof.

Of course, it is possible that the pre-treatment preparation, as is the case with known such preparations, consists of a plurality of components to be applied to said surfaces in succession or to be mixed immediately before application. In such a case the solid bodies comprising the second thermoplastic material are advantageously added to one of the components, or a mixture of a part of the components, or are mixed therewith immediately before the preparatory treatment.

The element surface 6 to be brought into contact with the pre-treated surface consists at least partly of the first thermoplastic material and, for friction or ultrasonic welding advantageously comprises energy directors 7 in the shape of e.g. ribs or humps. When this surface 6 is in close contact with the pre-treated surface, i.e. the cured pre-treatment preparation 1.1, and the element 5 is vibrated (twin arrow V) by means of a suitable tool (e.g. sonotrode of an ultrasonic device), the two thermoplastic materials are fused together. Any thin layer of non-thermoplastic components of the cured pre-treatment preparation 1.1 is obviously scraped off, broken up, or removed in some other manner from the solid bodies 2 beforehand and therefore do not appear to impede the welding in any way.

If the pre-treatment preparation is a correspondingly modified bone cement, the layer of cured pre-treatment compound 1.1 may be able to level out rough areas of an osseous surface but, as it is cured prior to the positioning of the element to be fastened, it cannot compensate for any irregularities in the element surfaces 6. This is not necessary, however, as such irregularities are automatically cancelled out during the welding process when the surface material of the element 5 is at least partly liquefied.

The set for carrying out the method according to FIGS. 1*a*-1*d* comprises e.g. the element 5 and of the pre-treatment preparation only the solid bodies 2 comprising the second thermoplastic material. Information concerning further components of the pre-treatment preparation, which are e.g. commercially available and familiar to the expert, as well as guidance with regard to the ratio in which the solid bodies are to be admixed to which components of such preparation, are further enclosed. It is also possible for the set to comprise all components of the pre-treatment preparation, wherein the solid bodies are admixed to at least one component of the preparation or are packaged separately, and wherein the other components of the pre-treatment preparation are already mixed together or are provided in part-mixtures for a successive application and/or for mixing immediately before application.

If applicable, the set also contains a tool (e.g. sonotrode for an ultrasonic device) adapted to the element 5, which is suitable for impinging the element 5 with mechanical vibrations.

FIGS. 2*a*-2*e* show a second exemplary embodiment of the method according to the invention. This method differs from the embodiment according to FIGS. 1*a*-1*d*, in particular, in the shape of the solid bodies comprising the second thermoplastic material. This specific form of solid bodies allows for them to be used separately from the other components of the pre-treatment preparation, i.e. to be brought into contact with the other components of the pre-treatment preparation in situ.

The solid bodies 2 comprising the second thermoplastic material are, in the method according to FIGS. 2*a*-2*e*, combined to form a flat, e.g. textile item, e.g. a woven item as illustrated. The flat item may also be e.g. a fleece or a perforated sheeting. This flat item is positioned on the surface 3 of dentine, tooth enamel, bone tissue, or a corresponding substitute material and if necessary temporarily fastened by suitable means (e.g. adhesive points, small implants e.g. similar to staples). Before or after positioning the flat item, further components of the pre-treatment preparation are also applied, wherein—particularly in the case of subsequent application—care is to be taken that these further components reach the surface 3 of dentine, tooth enamel, bone tissue, or a corresponding substitute material, through the flat item.

The yarn comprised in the textile item is e.g. a monofilament having a thickness of 10 to 100 μm, or it comprises a plurality of filaments. The mesh size is between 10 and 500 μm, wherein on the one hand a sufficient density of welding points is to be achieved, and on the other hand the textile item may have to be penetrable by further components of the pretreatment preparation.

Figures 2A, 2B, 2C, 2D:
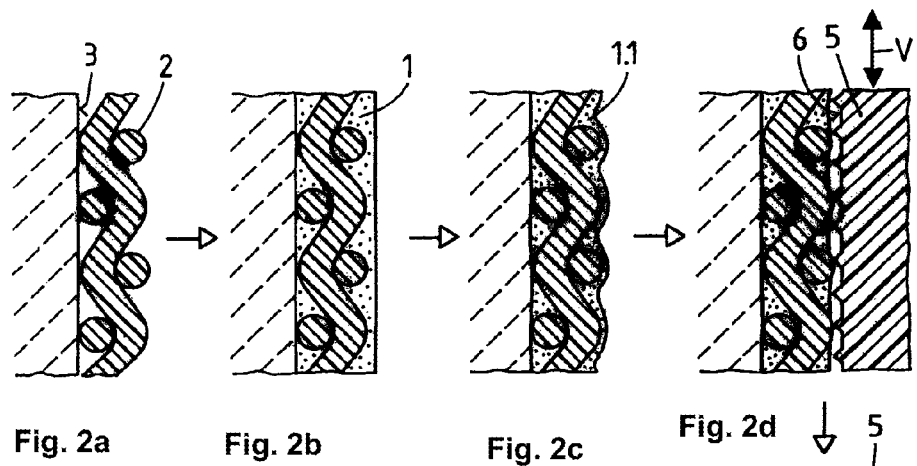
FIG. 2a shows, in section, solid bodies woven to a flat item on a surface of dentine.
FIG. 2b shows, in section, a pre-treatment preparation comprising the solid bodies woven to a flat item applied to the surface of a dental dentine.
FIG. 2c shows, in section, the pre-treatment preparation of FIG. 2b applied to the surface of a dental dentine after the step of curing.
FIG. 2d shows, in section, the cured pre-treatment preparation and an element to be affixed to the dentine.
Figure 2E:
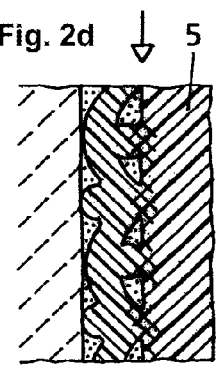
FIG. 2e shows, in section, the cured pre-treatment preparation and the affixed element.

When all components of the pre-treatment preparation are applied, the method is completed as described in connection with FIGS. 1*a*-1*d*. As shown in FIGS. 2*d*-2*e*, the welding process may lead, in addition to a welding between solid bodies 2 and element surfaces 6, to a further welding between individual solid bodies 2, e.g. between threads or filaments of a weave or fleece.

Of course, it is also possible to impregnate the flat item comprising the solid bodies with the other components of the pre-treatment preparation, or with at least a part thereof, prior to its positioning and to store and apply it in this impregnated form.

In the method as illustrated in FIG. 2, the flat item of the solid bodies comprising the second thermoplastic material consists e.g. of filaments (as illustrated), which in turn consist entirely of the second thermoplastic material. However, it is also conceivable that such filaments comprise a core of a different material (e.g. metal, ceramics, carbon fiber, etc.) which is coated with the second thermoplastic material. Thus, the flat item gains a stability, which allows for it to take over additional functions. It is e.g. possible to reinforce, or even partly replace, the walls of a tooth rendered rather thin by drilling.

In the same manner, it is possible to construct three-dimensional structures from several layers of the flat item described above and further components of the pre-treatment preparation, particularly the curable components thereof and to render them rigid through curing in situ, and then to fasten the element by welding on this structure. An example of such a three-dimensional structure is a bridge-like bearing structure extending from one prepared tooth across a gap to another prepared tooth, on which, after curing, a dental veneer is attached by mechanical vibration.

The set for carrying out the method as illustrated in FIGS. 2*a*-2*e* contains e.g. just the flat item (solid bodies 2 comprising the second thermoplastic material) and information regarding further, per se known and e.g. commercially available components for the pre-treatment preparation, regarding elements which are capable of being affixed using the flat item, in particular with regard to the first thermoplastic material, and regarding the use of vibrations for the affixation. The flat item is provided to dentists and surgeons e.g. in the shape of a tape, wherein a suitable length is severed from the tape and used depending on the application.

Here too, as described above in connection with the method as illustrated in FIGS. 1*a*-1*d*, it is possible that the set also contains the element to be affixed and/or further components of the pre-treatment preparation and a tool adapted to the element. Therein, the components of the pre-treatment preparation consist e.g. of a generally known primer system or primer compound or a generally known cement, which here too, can consist of two or more components to be mixed immediately before application or to be applied in succession. The flat item comprised in the set may also be impregnated with at least one other component of the pre-treatment preparation.

Figure 3:
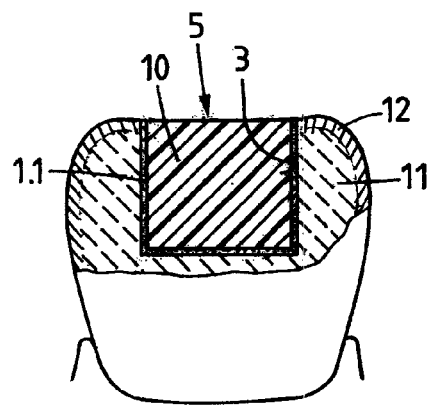
FIG. 3 shows an exemplary use of the method and set according to the invention

FIG. 3 shows an exemplary use of the method and set according to the invention. The element 5 to be affixed is a dental filling 10, which is to be fixed to surfaces 3 of dentine 11 and/or enamel 12 in a corresponding cavity. The tooth with the cavity and the element 5 placed in the cavity are shown in cross-section. Also shown, although exaggerated in its thickness, is the layer between the surface 3 and the filling 10, which comprises the cured pre-treatment compound 1.1.

The corresponding set contains e.g. the dental filling 10 comprising the first thermoplastic material, or possibly the material for the construction thereof, and the pre-treatment preparation, wherein the pre-treatment preparation may comprise one or more separate components and wherein the solid bodies are mixed with one of the components or are also provided separately.

Figure 4:
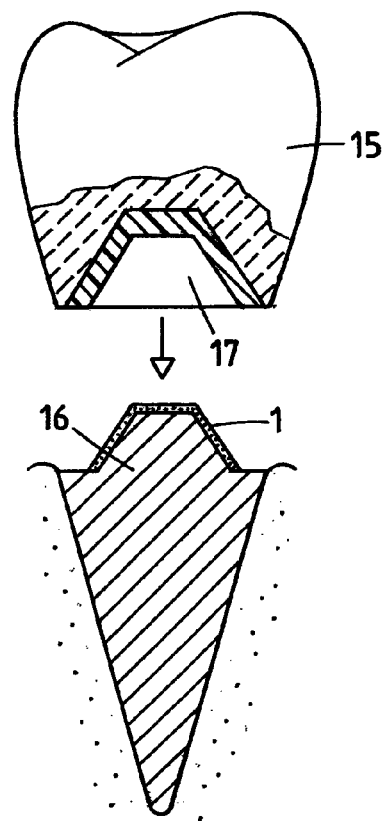
FIG. 4 shows another exemplary use of the method and set according to the invention.

FIG. 4 shows another exemplary use of method and set according to the invention. The element 5 to be affixed is a dental crown 15, which is to be mounted on a stump 16 or on a correspondingly designed dental implant of e.g. zirconiumoxide. Crown 15 and stump 16 are shown in cross-section. The cavity 17 of the crown 15 fitting over the stump 16 of the tooth or implant is coated with the first thermoplastic material or a composite material containing the first thermoplastic material. The stump 16 is treated with the pre-treatment preparation 1 in the manner described above.

A corresponding set contains e.g. the crown 15 and the pre-treatment preparation, which e.g. already contains the solid bodies comprising the second thermoplastic material in the form of particles. The set advantageously also comprises a tool adapted to the crown 15.

If the stump 16, which is to accommodate the crown, is the coronal end of an implant of e.g. zirconiumoxide, this implant may also be comprised in the set.

If the stump 16, which is to accommodate the crown, is part of a dental implant, it is also possible to equip the stump with the first thermoplastic material and to carry out the pre-treatment step of the method according to the invention in the cavity of the crown. In such a case it is possible to perform this preparatory treatment ex situ. However, the assembly of the two parts by welding, of which, in this case, the implant is in the sense of the invention the element to be affixed and the crown the substitute material, is always performed in situ.

Figure 5:
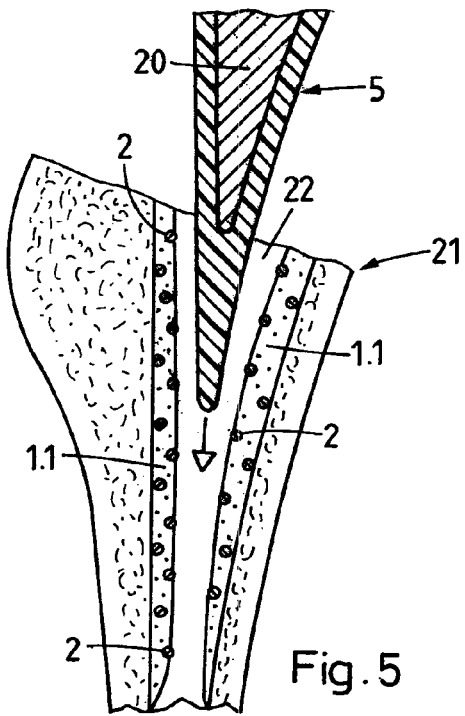
FIG. 5 shows yet another exemplary use of the method and set according to the invention.

FIG. 5 shows another exemplary use of the method and set according to the invention. The element 5 to be affixed is the shaft 20 of a hip-joint prosthesis to be secured in an appropriately prepared thighbone 21. Shaft and femur are only partially shown in cross-section. The preparation of the femur 21, in essence, comprises the steps of preparing the cavity 22 for the prosthesis shaft 20 and providing in this cavity a cured layer 1.1 of a known cement, wherein the cement has been modified with particles or thread-like items (solid bodies 2) comprising the second thermoplastic material (method according to FIG. 1) or wherein the cement is used in conjunction with a flat item (solid bodies 2) comprising the second thermoplastic material (method according to FIG. 2). The shaft 20 comprises e.g. a metallic core e.g. of a cobalt-chrome alloy and is at least partially coated with the first thermoplastic material or a composite material containing the first thermoplastic material.

Example

In teeth of pigs' carcasses a cavity (without recess) was created or the crown was removed to free the entrance to the root canal. A pre-treatment preparation was applied to the dentine and enamel surfaces of the cavities and root canals, which preparation had been produced by mixing a dental primer preparation on a methacrylate-basis (commercially available for use in conjunction with composite materials on a methacrylate-basis for filling dental cavities) and powdered polyamide. The pre-treatment preparation was cured in situ by UV light. Polyamide elements were then positioned in the pre-treated cavities and root canals and impinged with mechanical oscillation by means of a hand-held ultrasonic device.

In preliminary tests the force required to extract the polyamide elements were ranged around 15 N per $mm^2$ of bonding surface, which was between twice and four times more force than was necessary for the extraction of identical elements from identical cavities and root canals pre-treated with a preparation that did not contain any powdered polyamide.

The invention claimed is:

1. A method for affixing an element to a surface of dentine, tooth enamel, bone tissue, or a corresponding substitute material, the method comprising the steps of:
    a preparatory step in which a surface of dentine, tooth enamel, bone tissue, or a corresponding substitute material is pre-treated,
    a positioning step following the preparatory step in which surfaces of an element are brought into contact with the pre-treated surfaces, and
    a fixing step in which the element is affixed in situ to the pre-treated surface,
    wherein the element surfaces brought into contact with the pre-treated surface comprise at least in parts a first thermoplastic material,
    wherein, in the preparatory step, solid bodies comprising a second thermoplastic material are attached to said surfaces,
    wherein, in the preparatory step, a pre-treatment preparation comprising the solid bodies and at least one curable component is applied to said surfaces in a liquid or paste-like condition and wherein the pre-treatment preparation is then at least partly cured,
    wherein the first and the second thermoplastic material are capable of being welded together, and
    wherein, in the fixing step, the solid bodies attached to said surfaces are connected with the element surfaces by welding.

2. Method according to claim 1, wherein the preparatory step is performed in situ.

3. Method according to claim 1, wherein heat necessary for the welding is created by friction, irradiation or induction.

4. Method according to claim 3, wherein the friction is created by ultrasonic vibration applied to the positioned element.

5. Method according to claim 4, wherein the ultrasonic vibration is coupled into the element by means of a sonotrode.

6. Method according to claim 4, wherein the ultrasonic vibration has a frequency of 2 to 200 kHz.

7. Method according to claim 1, wherein the curable component of the pre-treatment preparation is a cross-linkable polymer or a polymer, ceramic, or hydraulic cement.

8. Method according to claim 1, wherein the solid bodies comprising the second thermoplastic material are applied to said surfaces together with at least one component of the pre-treatment preparation.

9. Method according to claim 1, wherein the solid bodies comprising the second thermoplastic material are applied to said surfaces separately from the at least one component of the pre-treatment preparation.

10. Method according to claim 1, wherein the solid bodies comprising the second thermoplastic material are particles or fibers or have the shape of a flat item.

11. Method according to claim 10, wherein the flat item is a textile structure.

12. Method according to claim 1, wherein the solid bodies comprising the second thermoplastic material consist entirely of the second thermoplastic material, consist of a composite material comprising the second thermoplastic material, or are coated with the second thermoplastic material.

13. Method according to claim 1, wherein the smallest dimensions of the solid bodies comprising the second thermoplastic material are at least 2 µm.

14. Method according to claim 1, wherein the first thermoplastic material is the same polymer as the second thermoplastic material.

15. Method according to claim 1, wherein the first and the second thermoplastic materials are polyamide.

16. Method according to claim 1, wherein the element to be affixed is a dental filling, an inlay, a dental veneer, a root pin, a piece of jewellery to be attached to a tooth, an implant to be implanted in bone tissue, an endoprosthesis, or an element with a therapeutic function to be attached to a bone.

17. Method according to claim 1, wherein said surfaces consist of a substitute material and wherein the preparatory step is performed ex situ.

18. Method according to claim 17, wherein the element to be affixed is an implanted dental implant and the named surfaces are situated in a cavity of a dental crown.

19. Set for affixing an element to a surface of dentine, tooth enamel, bone tissue, or a corresponding substitute material, the set comprising the element to be affixed and a pre-treatment preparation, wherein the element comprises element surfaces to be brought into contact with surfaces of dentine, tooth enamel, bone tissue, or a corresponding substitute material and a first thermoplastic material constituting at least part of said surfaces, wherein the pre-treatment preparation comprises solid bodies in the form of particles, fibers, a textile item, a fleece or a perforated sheeting and comprising a second thermoplastic material, wherein the pre-treatment preparation further comprises a curable component suitable for attaching the solid bodies to said surfaces, wherein the first and the second thermoplastic materials are capable to be welded together, and wherein at least one of the solid bodies, the curable component and the further components of the pre-treatment preparation are replaced by corresponding information.

20. Set according to claim 19, wherein the pre-treatment compound comprises the solid bodies and a per se known primer preparation or a bone cement, which comprises the curable component.

21. Set according to claim 19, wherein said at least one curable component is a cross-linkable polymer or a polymer, ceramic, or hydraulic cement.

22. Set according to claim 19, wherein the solid bodies are mixed with the curable component and/or with further components of the pre-treatment preparation.

23. Set according to claim 19, wherein the solid bodies are comprised in the set separately from the curable component and/or from further components of the pre-treatment preparation.

24. Set according to claim 19, further comprising a tool for impinging the element with mechanical vibrations.

25. Set according to claim 19, wherein the element is a dental filling, an inlay, a dental veneer, a root pin, a piece of jewellery to be fixed to a tooth, an implant to be implanted in bone tissue, an endoprosthesis, or an element with a therapeutic function to be attached to bone tissue.

* * * * *